United States Patent [19]
Thuresson

[11] Patent Number: 6,077,887
[45] Date of Patent: Jun. 20, 2000

[54] POLYELECTROLYTE COMPOSITION

[75] Inventor: Krister Thuresson, Lund, Sweden

[73] Assignee: Akzo Nobel Surface Chemistry AB, Stenungsund, Sweden

[21] Appl. No.: 09/084,696

[22] Filed: May 26, 1998

Related U.S. Application Data

[63] Continuation of application No. PCT/SE96/01503, Nov. 20, 1996.

[30] Foreign Application Priority Data

Nov. 29, 1995 [SE] Sweden .................................. 9504257

[51] Int. Cl.$^7$ .................................................. A61K 31/495
[52] U.S. Cl. ........................... 524/42; 429/188; 429/190; 429/191; 429/192; 525/54.1; 525/54.21; 525/54.24; 525/54.4
[58] Field of Search .............................. 524/42; 525/54.1, 525/54.21, 54.24, 54.4; 429/188, 190, 191, 192; 252/62.2

[56] References Cited

U.S. PATENT DOCUMENTS

| | | |
|---|---|---|
| 3,739,848 | 6/1973 | Lawson et al. .......................... 166/274 |
| 3,902,958 | 9/1975 | Breen et al. ............................. 162/164 |
| 4,780,517 | 10/1988 | Ching ....................................... 526/240 |
| 4,839,166 | 6/1989 | Grollier et al. ........................... 424/71 |
| 4,970,260 | 11/1990 | Lundberg et al. ...................... 524/516 |
| 5,578,598 | 11/1996 | Abe et al. ................................ 514/255 |
| 5,658,915 | 8/1997 | Abe et al. ................................ 514/255 |

FOREIGN PATENT DOCUMENTS

| | | |
|---|---|---|
| 0 130 732 | 1/1985 | European Pat. Off. . |
| 0 390 240 | 10/1990 | European Pat. Off. . |
| 33 02 456 | 7/1984 | Germany . |
| wo 94/06840 | 3/1994 | WIPO . |

*Primary Examiner*—Nathan M. Nutter
*Attorney, Agent, or Firm*—Ralph J. Mancini; Joan M. McGillycuddy

[57] ABSTRACT

An aqueous composition is described, which is characterised in that it comprises comprises a water-soluble electrolyte complex containing a combination of a water-soluble, anionic polyelectrolyte with hydrophobic groups having 6–30 carbon atoms, and a water-soluble cationic polyelectrolyte with hydrophobic groups having 6–30 carbon atoms. The polyelectrolyte composition can be used as thickening agent in water-based systems, such as paints, coating slips, cosmetics or cleaning compositions, and as water-binding agent in sanitary products, e.g. nappies, sanitary towels and the like.

11 Claims, 1 Drawing Sheet

POLYELECTROLYTE COMPOSITION

This is a continuation of International Application Number PCT/SE96/01503, which designated the United States and was filed on Nov. 20, 1996.

FIELD OF THE INVENTION

The present invention relates to a polyelectrolyte composition and the use thereof as thickening agent or water-binding agent.

BACKGROUND OF THE INVENTION

It is known to use nonionic as well as ionic polymers as thickening agents in water-based systems. Among the ionic polymers, both anionic and cationic polymers or polyelectrolytes are known. By a polyelectrolyte is here meant a polymer having a plurality of charged or ionizable groups, an anionic polyelectrolyte containing negatively charged groups and a cationic polyelectrolyte containing positively charged groups. It is also known to combine anionic and cationic polyelectrolytes.

By providing a nonionic or an ionic polymer with hydrophobic groups, these properties can be modified.

As an example of prior-art technique, the following documents can be mentioned.

EP 0 390 240 discloses nonionic cellulose ethers which are usable as thickening agents for water-based paints. The cellulose ethers are modified with pendent groups containing both hydrophobic and hydrophilic elements.

WO 94/06840 discloses a thickening agent for water-based paints, which consists of a water-soluble polyurethane of the so-called comb polymer type. The polyurethane has water-soluble oxyethylene groups and hydrophobic groups having 8–22 carbon atoms coupled to the main polymer chain.

U.S. Pat. No. 4,839,166 relates to a thickening agent resulting from the interaction on the one hand of a copolymer of cellulose or of a cellulose derivative which is grafted with a quaternary ammonium salt of a water-soluble monomer and, on the other hand, of a carboxylic anionic polymer. As a particularly preferred example of the cationic polymer, mention is made of hydroxyethyl cellulose copolymer grafted with diallyldimethylammonium chloride. As especially preferred examples of the anionic polymer, mention is made of copolymers of methacrylic acid with methyl methacrylate, monoethyl maleate, butyl methacrylate or maleic acid. Neither the cationic polymer nor the anionic polymer contains any hydrophobic groups.

DE 33 02 456 discloses the production of a cationic cellulose derivative and its use as conditioning agent in cosmetics in combination with anionic surfactants. The cationic cellulose derivative is obtained by quaternarisation of a cellulose ether containing dialkyl aminoalkyl ether groups, the alkyl parts having 1–4 carbon atoms. No combination of a cationic polymer and an anionic polymer is disclosed, nor a combination of such polymers as contain hydrophobic groups.

EP 0 130 732 relates to a water-soluble composition containing a particular anionic polymer and at least one cationic or amphoteric polymer which is selected among poly(diallyldimethylammonium chloride) and three further defined types of polymers. No modification of the anionic polymer and the cationic polymer with hydrophobic groups is stated. The described composition is intended to be used as thickening agent when treating subterranean formations such as wells.

U.S. Pat. No. 4,970,260 discloses a thickening agent for salt-containing aqueous solutions, which is based on a polymer complex of a water-soluble, anionic polymer having a low charge density and a water-soluble, cationic polymer having a low charge density, one of the polymers being present in an excess of at least about 20 mole % above the other. None of the two ionic polymers contains modifying hydrophobic groups.

U.S. Pat. No. 3,902,958 discloses a liquid dispersion containing a water-soluble anionic vinyl addition polymer and a water-soluble cationic polymer. The dispersion is used as additive in papermaking. Preferred examples of ionic polymers do not comprise polymers which are modified with hydrophobic groups, and no combination of anionic and cationic polymers which are modified with hydrophobic groups is disclosed.

An aqueous solution containing two different polymers normally separates in two phases. The phase separation can either result in both polymers separating in different phases, or it is possible to obtain an increased concentration of both polymers in a phase that is present together with a solvent-rich phase. The first phenomenon is called segregative phase separation and is usually observed in nonionic polymers or polyelectrolytes of the same charge and the corresponding charge density. The second phenomenon is called associative phase separation and occurs in mixtures of polyelectrolytes of opposite charge. Such an associative phase separation often takes place over practically the entire mixing range of both polyelectrolytes.

SUMMARY OF THE INVENTION

According to the present invention, it has now surprisingly been found that the above-mentioned associative phase separation between two polyelectrolytes of different charge can essentially be eliminated, and a synergistic viscosity increase can be accomplished if both the anionic and the cationic polyelectrolyte is hydrophobically modified. More specifically, the present invention provides an aqueous composition, characterised in that it comprises a water-soluble electrolyte complex containing a combination of a water-soluble, anionic polyelectrolyte with hydrophobic groups having 6–30 carbon atoms, and a water-soluble cationic polyelectrolyte with hydrophobic groups having 6–30 carbon atoms.

DETAILED DESCRIPTION OF THE INVENTION

Figure 1:
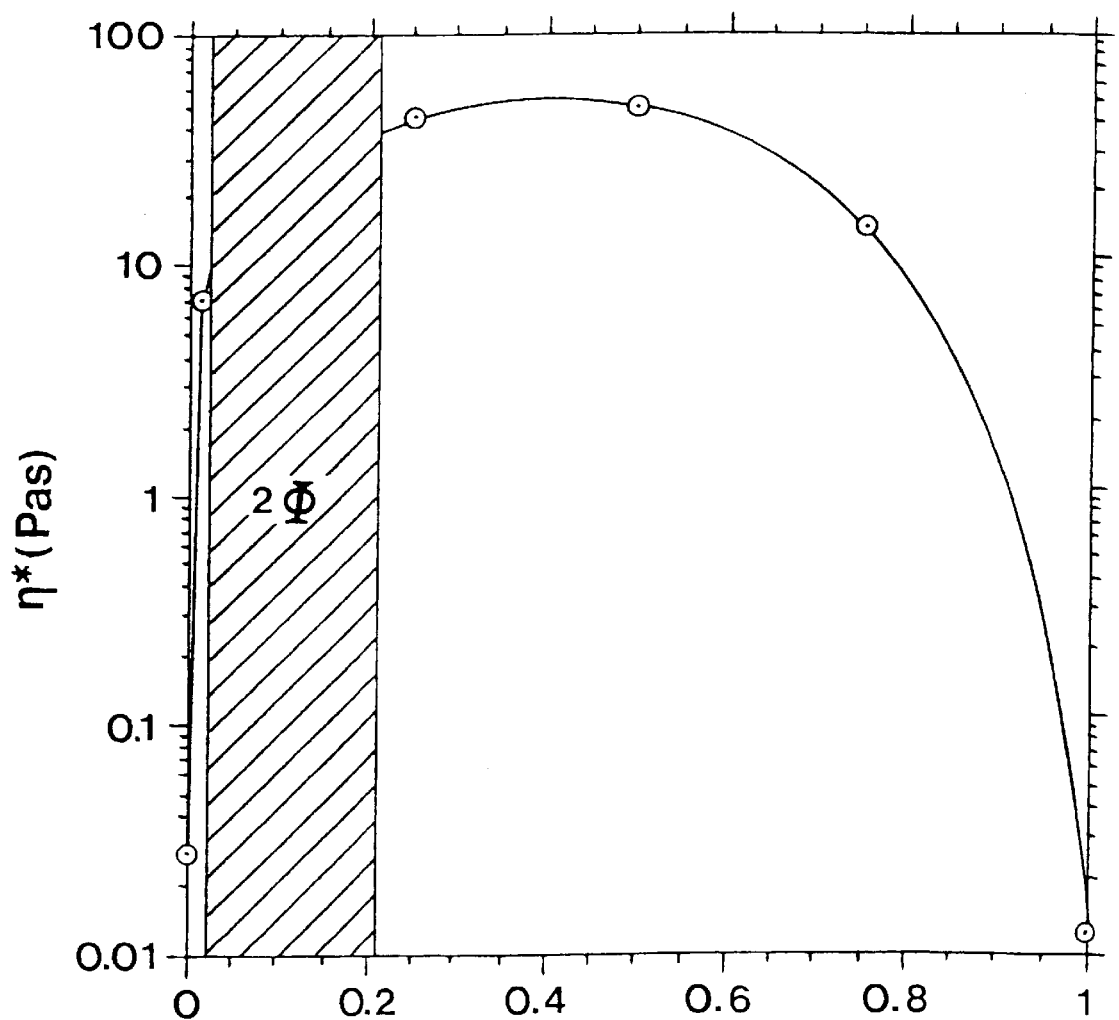
FIG. 1 shows viscosities of the inventive polyelectrolyte compositions stated in Example 1.

The present invention generally relates to an aqueous composition, which comprises a water-soluble electrolyte complex containing a combination of a water-soluble, anionic polyelectrolyte with hydrophobic groups having 6–30 carbon atoms, and a water-soluble cationic polyelectrolyte with hydrophobic groups having 6–30 carbon atoms.

A special aspect of the invention concerns the use of the polyelectrolyte composition in water-based systems as thickening agent (e.g. in paints, coating slips, cosmetics or cleaning compositions) and/or as water-binding agent (e.g. in nappies, sanitary towels or other sanitary products).

Further characteristics and advantages of the invention will appear from the following description and the appended claims.

As stated above, the polyelectrolyte composition comprises a component consisting of a water-soluble, anionic polyelectrolyte having hydrophobic groups. By the condition that the polyelectrolyte is water-soluble is meant that it is soluble in water at 25 C in a concentration of at least about 0.1% by weight, preferably at least about 0.5% by weight, more preferred at least about 1% by weight. The anionic polyelectrolyte consists of polymer molecules, each containing a plurality of negatively charged ionic groups. The polymer molecules may have a straight or branched main chain (back-bone), and the ionic groups may be present in the main chain or as pendent groups of the main chain. The anionic groups can be selected among existing anionic groups, such as carboxylate groups, sulphate groups, sulphonate groups, phosphate groups and phosphonate groups, carboxylate groups and sulphonate groups being preferred. The main polymer chain may consist of or contain different types of polymerisable monomers, such as vinyl alcohol, isocyanate, (meth)acrylate, acrylamide, alkylene oxide, alkylene oxide adducts, and carbohydrates, such as cellulose and cellulose derivatives. Among these, cellulose derivatives and acrylate-containing polymers are preferred. The molecular weight of the anionic polyelectrolyte may vary, but should be at least about 5,000, preferably at least about 10,000. Usually, the molecular weight is in the range of about 50,000–500,000. The anionic polyelectrolyte should further contain hydrophobic groups having 6–30 carbon atoms, preferably 8–22 carbon atoms. These hydrophobic groups may be straight or branched, saturated or unsaturated, aliphatic, cycloaliphatic or aromatic. Specific examples of such groups are decyl, dodecyl, tetradecyl, hexadecyl, butyl phenyl, octyl phenyl, nonyl phenyl, and dodecyl phenyl. The hydrophobic groups may preferably consist of or be included in side chains of the main polymer chain, but may also be included as segments of the main polymer chain. Optionally, the hydrophobic groups can be combined with the ionic groups such that the hydrophobic groups are present in connection with the ionic groups.

As also mentioned above, the polyelectrolyte composition according to the invention comprises a second component consisting of a water-soluble cationic polyelectrolyte having hydrophobic groups.

The water solubility condition for the cationic polyelectrolyte is the same as stated above for the anionic polyelectrolyte, i.e. it should be soluble in water at 25 in a concentration of at least about 0.1% by weight, preferably at least about 0.5% by weight, more preferred at least about 1% by weight. The cationic polyelectrolyte consists of polymer molecules, each containing a plurality of positively charged ionic groups. The polymer molecules may have a straight or branched main chain, and the ionic groups may be present in the main chain or as pendent groups of the main chain. The cationic groups can be selected from existing cationic groups, quaternary ammonium groups normally being preferred to primary, secondary and tertiary ammonium groups owing to the pH sensitivity of the latter. The main polymer chain may consist of or include different types of polymerisable monomers, such as vinyl alcohol, isocyanate, acrylamide, alkylene oxide, alkylene oxide adducts, and carbohydrates, such as cellulose and cellulose derivatives. Among these, cellulose derivatives and acrylamide-containing polymers are preferred. The molecular weight of the cationic polyelectrolyte may vary, but should be at least about 5,000, preferably at least about 10,000. Usually, the molecular weight is in the range of about 50,000–500,000. The cationic polyelectrolyte should further contain hydrophobic groups having 6–30 carbon atoms, preferably 8–22 carbon atoms. These hydrophobic groups can be straight or branched, saturated or unsaturated, aliphatic, cycloaliphatic or aromatic. Specific examples of such groups are decyl, dodecyl, tetradecyl, hexadecyl, butyl phenyl, octyl phenyl, nonyl phenyl, and dodecyl phenyl. The hydrophobic groups may preferably constitute or be included in side chains of the main polymer chain, but may also be included as segments of the main polymer chain. Optionally, the hydrophobic groups may be combined with the ionic groups such that the hydrophobic groups are present in connection with the ionic groups.

As is apparent from that stated above, there are a great number of different possibilities in the designing of the anionic and the cationic polyelectrolyte. Thus, the charge density may vary from essentially a small number of charges per polymer molecule and upwards. Moreover, the anionic and the cationic polyelectrolyte may have the same or different charge density. The hydrophobic degree, i.e. the number of hydrophobic groups of the polyelectrolytes, may essentially vary from one hydrophobic group per polyelectrolyte molecule and upwards, even if two of more hydrophobic groups are preferred. An upper limit of the number of hydrophobic groups is set by the condition that the polyelectrolyte should be water-soluble.

As examples of currently preferred types of polyelectrolytes according to the invention, the following may be mentioned.

An anionic polyelectrolyte containing hydrophobic groups in the form of a copolymer of acrylate and acrylamide, which is substituted with an alkyl group on the amide nitrogen. More specifically, this polyelectrolyte contains the segments

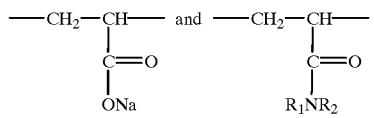

wherein $R_1$ is hydrogen or a hydrocarbon group, and $R_2$ is a hydrocarbon group, the total number of carbon atoms in $R_1$ and $R_2$ being 6–30 carbon atoms.

Another type of anionic polyelectrolyte is a hydrophobic cellulose derivative in the form of carboxymethyl cellulose (CMC) containing hydrophobic alkyl groups having 6–30 carbon atoms, preferably 12–24 carbon atoms.

A cationic polyelectrolyte containing hydrophobic groups consists of a water-soluble cellulose ether containing substituents of the formula

wherein $R_4$ is a hydrocarbon group having 6–30 carbon atoms, $R_5$ is a hydroxyalkyl group having 2–4 carbon atoms or an alkyl group, and $R_6$ has the same significance as $R_4$ or $R_5$. The cellulose ether can be, for instance, hydroxyethyl cellulose, and $R_4$ can be a dodecyl group, and $R_5$ and $R_6$ can be methyl groups. In this polyelectrolyte, the charges are positioned in the side chains of the hydrophobic groups.

A further polyelectrolyte consists of a polymer having a main chain containing water-soluble segments of polyoxyalkylene, the oxyalkylene segments preferably being derived to at least 50% from ethylene oxide, interrupted by segments containing ionic groups, hydrophobic uncharged segments having 6–30 carbon atoms, and/or charged ionic segments containing hydrophobic groups having 6–30 carbon atoms. A special example of a cationic polyelectrolyte of this type is a polymer of the formula

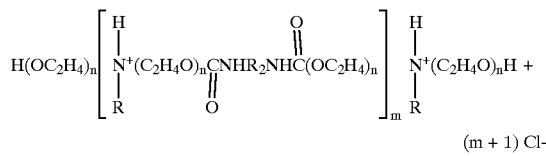

(m + 1) Clwherein R is a hydrocarbon group having 8–30 carbon atoms, $R_2$ is a hydrocarbon group having 1–30 carbon atoms, n is a number of 20–140, and m is a number of 1–50.

As stated above, the inventive combination of the defined anionic and cationic polyelectrolytes surprisingly results in the associative phase separation, that is normally obtained when mixing anionic and cationic polyelectrolytes, being reduced to a considerable extent in the mixing range. Besides, a synergistic and very great viscosity increase is unexpectedly obtained, which is in the order of 3–4 orders of magnitude when combining the hydrophobically modified polyelectrolytes according to the invention.

Without commitment to a particular theory, it is assumed that the reasons of these effects are as follows.

A mixture of an anionic and a cationic polyelectrolyte without modifying hydrophobic groups has a strong tendency to associative phase separation, which results in two phases, i.e. a precipitation, within almost the entire mixing range of the two polyelectrolytes. The same applies if one of the polyelectrolytes is hydrophobically modified. If, however, both polyelectrolytes are hydrophobically modified, a decrease of the two-phase area arises, implying that the two polyelectrolytes can be mixed in almost any proportions whatever, without a precipitation taking place. This may be found contradictory since the hydrophobic modification of the polyelectrolytes on the one hand results in a decrease of the solubility of the individual polyelectrolyte and, on the other hand, should result in an increased attraction between the polyelectrolytes, i.e. an increased tendency to associative phase separation. The fact that the combination of the two polyelectrolytes having modifying hydrophobic groups, contrary to what could be expected, has a decreased tendency to associative phase separation may be explained by interaction between the two polyelectrolytes. Since the two polyelectrolytes have charges of opposite sign and besides are provided with hydrophobic groups, the interaction between the polyelectrolytes can be of electrostatic or hydrophobic nature as well as a combination thereof. In the hydrophobic interaction, the electrostatic charges will probably have such an effect that it is preferably hydrophobic groups in polyelectrolytes of different charges that interact. In the interaction between the two hydrophobically modified polyelectrolytes, a complex forms, which normally has a net charge and is hydrophilic, i.e. water-soluble. It is only when there is such a mixing ratio between the polyelectrolytes that charge neutrality is attained that there is a considerable risk of phase separation, i.e. precipitation takes place. The presence of a considerable amount of hydrophilic groups, however, may prevent phase separation. Depending on whether the two polyelectrolytes have the same or different charge density, charge neutrality is attained for the polymer complex in the centre of the mixing range or with displacement towards one end of the mixing range. When there is charge neutrality, the polymer complex of the anionic and the cationic polyelectrolyte has the net charge zero, in which case the complex normally precipitates such that two phases are obtained, a water-rich phase and a precipitation phase. When adding a further amount of one polyelectrolyte, this will increase the charge of the precipitated polymer complex, which swells until it has reached a sufficient net charge for absorbing the entire solution, i.e. the precipitate has been dissolved and there is only one phase. For this reason, the inventive electrolyte complex should have a net charge, and this net charge should be at least 5%, preferably between 15 and 99%, most advantageously between 30 and 97% of the total number of charges of the electrolyte complex.

The presence of one or more ionic tensides, that is to say compounds having a hydrophobic part and a hydrophilic ionic part, may also be included in the complex. Depending on whether the ionic tenside or tensides have a positive or negative net charge, they can displace the net charge of the complex in one direction or the other. The solubility of a complex containing ionic tensides is affected by the same basic principles as apply to a complex consisting merely of an anionic and a cationic polyelectrolyte.

Even if the invention is not limited to any particular proportions between the anionic and the cationic polyelectrolyte and tensides, if any, the proportions should be such that the two polyelectrolytes form a water-soluble complex, i.e. a one phase mixture, since especially in this case the advantages of the invention are achieved.

Regarding the unexpectedly high viscosity increase when combining, according to the invention, an anionic and a cationic polyelectrolyte containing modifying hydrophobic groups, this is assumed to be caused by the following. By the polyelectrolytes containing hydrophobic groups, these tend to be coupled to each other while forming a three-dimensional network. The hydrophobic interaction is unselective, but since the polyelectrolytes further contain charged ionic groups, the interaction preferably takes place between hydrophobic groups included in polyelectrolytes of opposite charge. This strengthens the network since both hydrophobic and electrostatic forces contribute. The strength of the electrostatic contribution may also possibly be favoured by an increased local charge concentration caused by aggregation of hydrophobic groups included in one of the polyelectrolytes. These three factors coact to form a very stable network and, consequently, a high viscosity.

The polyelectrolyte compositions according to the invention have a large number of different fields of application, utilising the advantages that high viscosities can be achieved with a small addition of polyelectrolyte and that the risk of phase separation is reduced to a great extent. Among especially preferred fields of application, mention can be made of thickening agents in water-based paints, thickening agents in the papermaking industry, for instance in coating slips, thickening agents in cosmetics and water-absorbing agents in sanitary products such as nappies, sanitary towels and the like.

To facilitate the understanding of the invention, some Examples are given below, which are only intended to be elucidative and do not restrict the scope of the invention. In the Examples, all parts and percentages relate to weight, unless otherwise stated.

EXAMPLE 1

In this Example, a commercial N,N-dimethyl-N-dodecyl ammonium derivative of hydroxyethyl cellulose (LM200 supplied by Union Carbide Chemicals and Plastics Company, Inc. Terrytown, USA) was used as cationic polyelectrolyte. This cationic cellulose derivative has a molecular weight of about 100000 and the hydrophobic degree of modification is 5.4 mole %. The charge concentration in a 1% by weight aqueous solution was 2 millimolal.

As anionic polyelectrolyte, use was made of a copolymer of acrylic acid and acrylamide, hydrophobic dodecyl groups being coupled to the amide nitrogen on the acrylamide units. The molecular weight of the anionic polyelectrolyte was about 150000, and the hydrophobic substitution rate was 3 mole %. Before being used, the polyelectrolyte was neutralised with NaOH and freeze-dried. The charge concentration in a 1% by weight aqueous solution was 99 millimolal.

A 1% solution of the anionic polyelectrolyte was successively added by titration to a 1% aqueous solution of the cationic polyelectrolyte LM200. First, the mixture was clear, i.e. there was a one-phase system, but when the mixture contained about 2.0% anionic polyelectrolyte, two phases formed by associative phase separation. In the continued adding of the anionic polyelectrolyte, the mixture reverted to the one-phase state when it contained 21% anionic polyelectrolyte, and the mixture continued to be one-phase when adding a further amount of the anionic polyelectrolyte.

For comparison, the above-mentioned mixing experiment was repeated, the anionic polyelectrolyte being replaced with an identical anionic polyelectrolyte, but without hydrophobically modifying dodecyl groups. In this mixing experiment, the mixture had two phases from about 1.7% to 99% of the anionic polyelectrolyte, i.e. within practically the entire mixing range there were two phases.

The above-described mixing experiment with the hydrophobically modified polyelectrolytes according to the invention was repeated, the complex viscosity of the mixture, *, at 0.1 Hz being measured by means of a Bohlin VOR rheometer in oscillation. The results are shown in the enclosed FIG. 1, where the value 0 on the axis of abscissa indicates that the mole fraction of the anionic polyelectrolyte is 0, i.e. the mixture consists of a 1% by weight solution of merely the cationic polyelectrolyte (LM200). Correspondingly, the value of the axis of abscissa indicates that the mole fraction of the anionic polyelectrolyte is 1, i.e. the mixture contains merely a 1% by weight solution of the anionic electrolyte. In FIG. 1, also the two-phase area has been indicated by dashed lines. As is apparent from FIG. 1, it is possible, in a combination of an anionic polyelectrolyte with hydrophobic groups and a cationic polyelectrolyte with hydrophobic groups, to reach a viscosity which is 3–4 orders of magnitude higher, i.e. almost 10000 times higher, than for one of the polyelectrolytes alone.

I claim:

1. An aqueous composition which comprises a water-soluble electrolyte complex containing a combination of a water-soluble, anionic polyelectrolyte with hydrophobic groups having 6–30 carbon atoms, and a water-soluble cationic polyelectrolyte with hydrophobic groups having 6–30 carbon atoms, wherein the electrolyte complex has a net charge of at least about 5% of the total number of charges of the electrolyte complex.

2. The aqueous composition of claim 1 wherein the electrolyte complex has a net charge of preferably between 15% and 99% of the total number of charges of the electrolyte complex.

3. The aqueous composition of claim 1 wherein the anionic groups of the electrolyte complex are selected from carboxylate groups, sulphate groups, sulphonate groups, phosphate groups and phosphonate groups or mixtures thereof, and that the cationic groups of the electrolyte complex are selected among primary, secondary, tertiary and quaternary ammonium groups or mixtures thereof.

4. The composition of claim 1 wherein the hydrophobic groups are formed as side chains of the main chain of the polyelectrolyte.

5. The composition of claim 1 wherein at least one of the polyelectrolytes has a polysaccharide chain, to which have been applied one or more of ionic hydrophilic groups, uncharged hydrophobic groups having 6–30 carbon atoms, and ionic hydrophobic groups having 6–30 carbon atoms.

6. The composition of claim 1 wherein the anionic polyelectrolyte consists of a water-soluble cellulose ether with carboxymethyl groups and hydrophobic groups having 6–30 carbon atoms.

7. The composition of claim 1 wherein the cationic polyelectrolyte consists of water-soluble cellulose ether containing substituents of the formula:

wherein $R_4$ is a hydrocarbon group having 6–30 carbon atoms, $R_5$ is a hydroxyalkyl group having 2–4 carbon atoms or an alkyl group, and $R_6$ has the same significance as $R_4$ or $R_5$.

8. The composition of claims 1 wherein the anionic polyelectrolyte consists of a polymer containing the segments

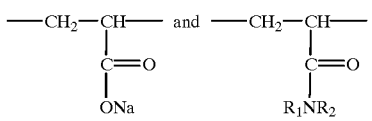

wherein $R_1$ is hydrogen or a hydrocarbon group, and $R_2$ is a hydrocarbon group, the total number of carbon atoms in $R_1$ and $R_2$ being 6–30 carbon atoms.

9. The composition of claim 1 wherein the cationic polyelectrolyte consists of a polymer of the formula

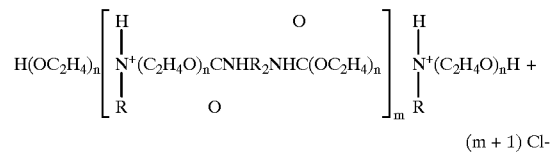

wherein R is a hydrocarbon group having 8–30 carbon atoms, $R_2$ is a hydrocarbon group having 1–30 carbon atoms, n is a number of 20–140, and m is a number of 1–50.

10. A thickening agent which comprises a water-based system containing an aqueous composition which comprises a water-soluble electrolyte complex-containing a combination of a water-soluble, anionic polyelectrolyte with hydrophobic groups having 6–30 carbon atoms, and a water-soluble cationic polyelectrolyte with hydrophobic groups having 6–30 carbon atoms, wherein the electrolyte complex has a net charge of at least about 5% of the total number of charges of the electrolyte complex.

11. A water-binding agent which comprises a water-based system containing an aqueous composition which comprises a water-soluble electrolyte complex containing a combination of a water-soluble, anionic polyelectrolyte with hydrophobic groups having 6–30 carbon atoms, and a water-soluble cationic polyelectrolyte with hydrophobic groups having 6–30 carbon atoms, wherein the electrolyte complex has a net charge of at least about 5% of the total number of charges of the electrolyte complex.

* * * * *